United States Patent
Hari

(10) Patent No.: US 11,622,515 B2
(45) Date of Patent: Apr. 11, 2023

(54) GENERATION OF NEW VARIETIES OF CANNABIS BY CHEMICAL MUTAGENESIS OF CANNABIS CELL SUSPENSIONS

(71) Applicant: Bright Green Corporation, Wilmington, DE (US)

(72) Inventor: V. Hari, Orlando, FL (US)

(73) Assignee: Bright Green Corporation, East Windsor (CA)

( * ) Notice: Subject to any disclaimer, the term of this patent is extended or adjusted under 35 U.S.C. 154(b) by 215 days.

(21) Appl. No.: 16/594,733

(22) Filed: Oct. 7, 2019

(65) Prior Publication Data

US 2020/0107510 A1 Apr. 9, 2020

Related U.S. Application Data

(60) Provisional application No. 62/741,704, filed on Oct. 5, 2018.

(51) Int. Cl.
*A01H 3/04* (2006.01)
*A01H 6/28* (2018.01)
*A01H 4/00* (2006.01)

(52) U.S. Cl.
CPC .............. *A01H 3/04* (2013.01); *A01H 4/005* (2013.01); *A01H 6/28* (2018.05)

(58) Field of Classification Search
CPC ...................................................... A01H 3/04
See application file for complete search history.

(56) References Cited

PUBLICATIONS

Hussein, S., (2014) (Thesis: Cannabinoids production in *Cannabis sativa* L.: An in vitro approach; Technical University of Dortmund, 138 pages. (Year: 2014).*
Adhikari, D. et al. Frontiers in Plant Science; published Mar. 3, 2021, vol. 12, article 627240, pp. 1-22. (Year: 2021).*
Patel, P. (Fall 2019) Honors Thesis: Middle Tennessee State University, 24 pages. (Year: 2019).*
Feeney and Punja (2003) In Vitro Cell Dev Biol.—Plant 39:578-585. (Year: 2003).*
Jones, R. Aug. 1979; Masters Thesis: Cell Culture, Protoplast isolation, and Cell Fusion of *Cannabis sativa* L., University of Houston pp. 1-80. (Year: 1979).*

* cited by examiner

*Primary Examiner* — Russell Kallis
(74) *Attorney, Agent, or Firm* — Carlson, Gaskey & Olds, P.C.

(57) ABSTRACT

An method of generating and selecting mutant Cannabis plants through mutagenesis of isolated Cannabis plant cells includes subjecting plant parts of one or more Cannabis plants to a pectinase treatment to obtain living cells of the one or more Cannabis plants, suspending the living cells in a mutagenic solution comprising methane sulfonate (EMS) and dimethyl sulfoxide (DMSO) to obtain mutated Cannabis cells, centrifuging the mutated Cannabis cells to obtain pelleted cells, and providing the pelleted cells on culture media.

14 Claims, No Drawings

GENERATION OF NEW VARIETIES OF CANNABIS BY CHEMICAL MUTAGENESIS OF CANNABIS CELL SUSPENSIONS

CROSS-REFERENCE TO RELATED APPLICATIONS

This application claims priority to U.S. Provisional Application No. 62/741,704 which was filed on Oct. 5, 2018, and is incorporated herein by reference in its entirety.

BACKGROUND

As Cannabis use becomes more accepted for medicinal and recreational purposes, there is a desire for strains of Cannabis that exhibit more desirable characteristics, such as Cannabinoid profile and/or tolerance to stress, salinity, temperature, etc. than are currently available.

SUMMARY

A method according to one aspect of the present disclosure includes subjecting plant parts of one or more Cannabis plants to a pectinase treatment to obtain living cells of the one or more Cannabis plants, suspending the living cells in a mutagenic solution comprising methane sulfonate (EMS) and dimethyl sulfoxide (DMSO) to obtain mutated Cannabis cells, centrifuging the mutated Cannabis cells to obtain pelleted cells, and providing the pelleted cells on culture media.

A method according to one aspect of the present disclosure includes subjecting plant parts of Cannabis plants to pectinase treatment, incubating the pectinase-treated plant parts at a first temperature in a first incubation, filtering the incubated plant parts to obtain filtrate-containing cells, and centrifuging the filtrate-containing cells in a first centrifuging operation. The method also includes suspending the centrifuged filtrate-containing cells in a mutagenic solution that includes methane sulfonate (EMS) and dimethyl sulfoxide (DMSO), incubating the mutagenic solution at a second temperature after said suspending in a second incubation to obtain mutated Cannabis cells, and centrifuging the mutagenic solution containing the mutated Cannabis cells in a second centrifuging operation to obtain pelleted cells. The pelleted cells are provided in a series of culture media.

The embodiments, examples, and alternatives of described in the claims and in the following description and drawings, including any of their various aspects or respective individual features, may be taken independently or in any combination. Features described in connection with one embodiment are applicable to all embodiments, unless such features are incompatible.

DETAILED DESCRIPTION

The present disclosure describes a protocol and method for selecting chemical mutants of Cannabis through a selection process involving mutagenesis of isolated cells of Cannabis by Ethyl methane sulfonate (EMS) or nitrous acid ($HNO_2$) through mutation breeding.

Chemical mutagenesis is a process whereby biological cells are exposed to chemical agents such as Ethyl methane sulfonate (EMS) and nitrous acid ($HNO_2$) in order to induce mutations in cells. Ethyl methane sulfonate is a powerful mutagenic agent that is used to generate new variant crops by treating seeds with this chemical. Likewise, $HNO_2$ is a well-known de-aminating mutagenic agent for generating mutant organisms. Mutant crop plants generated by EMS and $HNO_2$ treatment are not considered genetically modified organisms and do not have to undergo any legally mandated testing before being grown as crop plants and further such mutants are considered "organic."

Ethyl methane sulfonate (EMS) is a mutagenic and potentially carcinogenic organic compound. It produces random point mutations in genetic material by nucleotide substitution, particularly by guanine alkylation. These result in a transition whereby original G:C pairs in DNA are replaced by A:T base pairings. This changes the genetic information and alters gene expression such that new varieties of organisms treated with EMS can arise. Likewise, nitrous acid, which is an unstable weak acid, deaminates cytosine to uracil and adenine to hypoxanthine so that during DNA replication G:C pairs becomes A:T pairs and original A:T pairs become G:C pairs, which during transcription change the gene coding and change the amino acid sequences of proteins coded by the mutant regions.

No mutant variety of Cannabis has been generated or attempted using EMS or $HNO_2$ as mutagens. The present disclosure provides a technique for generation of Cannabis mutants through EMS and $HNO_2$ mutagenesis of plant cells. The technique includes the exposure of isolated plant cells to these mutagenic agents.

An illustrative example method for generating and selecting mutant Cannabis plants through mutagenesis of isolated Cannabis plant cells includes using Ethyl methane Sulfonate (EMS) and Nitrous acid ($HNO_2$). The term "Cannabis" includes *C. sativa, C. indica, C. ruderalis* and all their subspecies, varieties, strains, hybrids and bio-ecotypes.

The example method begins with a pectinase treatment of plant leaves or other organs to isolate living cells of cannabis. Young leaves or other plant parts, for example, are sliced into 1 $mm^2$ pieces and are vacuum-infiltrated with a 1 mg/ml solution of pectinase in an isotonic buffer. Those pieces are then incubated for three hours at 37° C. The separated cells are filtered through porous cheesecloth or porous filters and the filtrate-containing cells are centrifuged at 100 G for 10 minutes. The resultant pelleted cells are re-suspended in a solution of EMS and dimethyl sulfoxide (DMSO) and are incubated for three hours at 30° C.

In one example, the mutagenic solution is prepared as a 100 ml solution of 0.5% (v/v) EMS with 2% DMSO by mixing 2 ml of DMSO with 0.5 ml of EMS solution (d=1.17 g/ml) in 97.5 ml of distilled water. In some embodiments, the mutagenic solution includes $HNO_2$ prepared freshly by reacting sodium nitrite with hydrochloric acid to which DMSO is added in an isotonic buffer.

After incubation in the mutagenic solution, the cells which have been pelleted down by centrifugation are washed, diluted and plated onto callous culture media. Individual calli are transferred to root and shoot culture media or somatic embryogenesis media and are incubated. The resultant plantlets are transferred individually into larger culture media containers. After 4 to 6 inches of growth, the plants are transferred to 4-6 inch biodegradable pots containing soil and allowed to grow further. In one example, the biodegradable pots are at least partially composed of peat moss and wood pulp (e.g., JIFFY-POTS®).

After sufficient growth, the plants are examined for variability such as cannabinoid profile; growth profiles such as size, branching and height; water stress; salinity tolerance; temperature tolerance; flowering time; and other potentially valuable variant physiological and biochemical traits. Plants are selected based on the variability. The selected plants are propagated in the plant nursery and individual plants are further examined and evaluated. Mutants are maintained for germplasm and those with characteristics that are considered of commercial and medicinal value are propagated on a large scale for extraction of phytochemicals. The extracted phytochemicals include various ones of the 113 known cannabinoids which exhibit varied properties, such as THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), and CBL (cannabicyclol). In one example, the extracted phytochemicals are mixed in varying proportions. Initially, plants that have a short growth habitat, which allows for growth under hydroponic robot controlled green houses, with high ratios of CBD:THC or THC:CBD are selected (e.g., a ratio of CBD:THC above a first predefined threshold or a ratio of THC:CBD above a second predefined threshold).

The chemical mutagenesis technique described above may be carried out using a variety of chemical mutagens.

Although example embodiments have been disclosed, a worker of ordinary skill in this art would recognize that certain modifications would come within the scope of this disclosure. For that reason, the following claims should be studied to determine the scope and content of this disclosure.

What is claimed is:

1. A method for Cannabis plants, comprising:
   subjecting plant parts of one or more Cannabis plants to a pectinase treatment to obtain living cells of the one or more Cannabis plants;
   suspending the living cells in a mutagenic solution comprising methane sulfonate (EMS) and dimethyl sulfoxide (DMSO) to obtain mutated Cannabis cells;
   centrifuging the mutated Cannabis cells to obtain pelleted cells; and
   providing the pelleted cells on culture media.

2. The method of claim 1, comprising:
   cutting the plant parts pieces having an area of approximately 1 mm$^2$ prior to said subjecting the plant parts to the pectinase treatment.

3. The method of claim 2, comprising, after the subjecting and prior to the suspending:
   filtering the living cells through a porous filter to obtain filtrate-containing living cells, and
   centrifuging the filtrate-containing living cells at approximately 100 G for approximately 10 minutes to obtain pelleted living cells;
   wherein said suspending the living cells in the mutagenic solution comprises suspending the pelleted living cells in the mutagenic solution.

4. The method of claim 1, wherein said subjecting the plant parts to the pectinase treatment comprises:
   vacuum-infiltrating the plant parts with a solution of pectinase in an isotonic buffer; and
   incubating the pectinase solution and plant parts for approximately three hours at approximately 37° Celsius.

5. The method of claim 4, wherein the solution of pectinase in an isotonic buffer has a concentration of pectinase of approximately 1 mg/ml.

6. The method of claim 1, comprising:
   preparing the mutagenic solution as an approximately 100 ml solution of 0.5% (v/v) of EMS with 2% DMSO by mixing approximately 2 ml of DMSO with approximately 0.5 ml of EMS solution having a density of approximately 1.17 g/ml of EMS in approximately 97.5 ml of distilled water.

7. The method of claim 1, wherein the mutagenic solution includes nitrous acid.

8. The method of claim 7, comprising:
   preparing the nitrous acid by reacting sodium nitrite with hydrochloric acid.

9. The method of claim 1, comprising:
   washing and diluting the pelleted cells after the centrifuging and prior to providing the pelleted cells on the culture media.

10. The method of claim 1, wherein:
    said subjecting the plant parts to the pectinase treatment comprises incubating the pectinase solution and plant parts at a first temperature; and
    said suspending the living cells in a mutagenic solution comprises incubating the mutagenic solution and suspended living cells at a second temperature.

11. The method of claim 10, wherein the second temperature is lower than the first temperature.

12. The method of claim 11, wherein the first temperature is approximately 37° Celsius, and the second temperature is approximately 30° Celsius.

13. A method for Cannabis plants, comprising:
    subjecting plant parts of Cannabis plants to pectinase treatment;
    incubating the pectinase-treated plant parts at a first temperature in a first incubation;
    filtering the incubated plant parts to obtain filtrate-containing cells;
    centrifuging the filtrate-containing cells in a first centrifuging operation;
    suspending the centrifuged filtrate-containing cells in a mutagenic solution that includes methane sulfonate (EMS) and dimethyl sulfoxide (DMSO);
    incubating the mutagenic solution at a second temperature after said suspending in a second incubation to obtain mutated Cannabis cells;
    centrifuging the mutagenic solution containing the mutated Cannabis cells in a second centrifuging operation to obtain pelleted cells;
    providing the pelleted cells in a series of culture media.

14. The method of claim 13, wherein:
    said first incubation is performed at a first temperature; and
    said second incubation is performed at a second temperature that is lower than the first temperature.

* * * * *